United States Patent [19]
Graf et al.

[11] 4,450,277
[45] May 22, 1984

[54] PREPARATION OF 1-SUBSTITUTED IMIDAZOLES

[75] Inventors: Fritz Graf, Speyer; Leopold Hupfer, Friedelsheim, both of Fed. Rep. of Germany

[73] Assignee: BASF Aktiengesellschaft, Fed. Rep. of Germany

[21] Appl. No.: 190,901

[22] Filed: Sep. 25, 1980

[30] Foreign Application Priority Data

Oct. 8, 1979 [DE] Fed. Rep. of Germany ....... 2940709

[51] Int. Cl.³ .................. C07D 233/58; C07D 233/60; C07D 233/61
[52] U.S. Cl. .................................... 548/346; 548/335; 548/341; 548/342
[58] Field of Search ................ 548/335, 346, 341, 342

[56] References Cited

U.S. PATENT DOCUMENTS 3,037,028  5/1962  Green ................................... 548/335

OTHER PUBLICATIONS

Preliminary Brochure of BASF AG on 1- and 2-Methylimidazole and 1,2—Dimethylimidazole Dated 9/1967.
Lions, F., et al., J. Proc. Royal Soc. N.S.W., 74 (1941), pp. 365–372.

Primary Examiner—Richard A. Schwartz
Attorney, Agent, or Firm—Keil & Witherspoon

[57] ABSTRACT

A process for the preparation of 1-substituted imidazoles by reacting an α-dicarbonyl compound with ammonia, an aldehyde and a primary amine in an aqueous medium, in a single stage, at 20°–150° C.

3 Claims, No Drawings

PREPARATION OF 1-SUBSTITUTED IMIDAZOLES

The present invention relates to a novel process for the preparation of 1-substituted imidazoles.

1-substituted imidazoles, such as N-alkylimidazoles, can be prepared by catalytic alkylation of an imidazole with an alkanol at an elevated temperature and under superatmospheric pressure, or by reaction of an imidazole with an alkyl chloride. These processes require the N-unsubstituted imidazole as an intermediate.

It is an object of the present invention to provide a process which permits the direct preparation of N-substituted imidazoles in a single reaction stage.

It is true that attempts have already been made to prepare 1-substituted imidazoles from the starting materials for the synthesis of imidazole, such as diacetyl, ammonia, an aldehyde and an alkylamine, the Schiff base first being formed from diacetyl and the amine and then being reacted with the reaction product of the aldehyde and ammonia. However, in this process, described in J. Proc. Royal Soc. N.S.W. 74 (1941), 365–372, only low yields of the 1-substituted imidazoles are obtained.

We have found that the object stated above is achieved and that 1-substituted imidazoles may be prepared more advantageously, by a process wherein an α-dicarbonyl compound, ammonia, an aldehyde and a primary amine are reacted in an aqueous medium, in a single stage, at from 20° to 150° C.

Using the novel process, it is possible to prepare 1-substituted imidazoles which may also be substituted in positions 2, 4 and 5. Such compounds for example have the formula

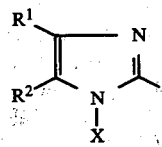

where $R^1$, $R^2$ and $R^3$ are hydrogens or aliphatic or aromatic radicals and X is an aliphatic, cycloaliphatic or aromatic radical.

Examples of suitable starting materials are α-dicarbonyl compounds of the formula $R^1$—CO—CO—$R^2$, where $R^1$ and $R^2$ have the above meanings. Examples of aliphatic radicals are unsubstituted and substituted straight-chain and branched alkyl of 1 to 5 carbon atoms. Examples of aromatic radicals are unsubstituted and substituted phenyl or naphthyl. Examples of substituents of the aliphatic and aromatic radicals are HO—, $H_3COOC$— and $H_3CO$— groups. Specific examples of suitable α-dicarbonyl compounds are glyoxal, diacetyl, benzil and methylglyoxal.

Examples of suitable aldehydes are compounds of the formula $R^3$—CHO, where $R^3$ has the above meanings. Examples of aliphatic radicals in the aldehydes are straight-chain and branched alkyl, for example of 1 to 8 carbon atoms, which may be substituted by, for example, phenyl or HO—, $H_3COOC$— or $H_3CO$— groups. Examples of aromatic radicals which may be present in the aldehydes are phenyl which is unsubstituted or substituted by alkyl or by HO— or $H_3COOC$— groups. Specific examples of suitable aldehydes are formaldehyde, acetaldehyde, propionaldehyde, isobutyraldehyde and benzaldehyde.

Examples of primary amines to be used as starting components are monoamines of the formula X—$NH_2$, of the aliphatic, cycloaliphatic or aromatic series. Suitable aliphatic radicals are straight-chain or branched saturated or unsaturated hydrocarbon radicals of 1 to 20 carbon atoms, which may, for example, be substituted by HO—, $(CH_3)NH$—, $(CH_3)_2N$—, $H_5C_2NH$—, $H_5C_2O$—, $H_3CO$— or ether groups. Examples of cycloaliphatic radicals are cyclohexyl and norbornyl. Examples of aromatic radicals are phenyl which may be substituted by $H_3CO$—, $(CH_3)_2N$—, $H_5C_2NH$— or $H_3COOC$— groups. Specific examples of suitable amines of the stated type are methylamine, ethylamine, propylamine, octylamine, dodecylamine, aniline, methoxyethylamine, ethoxyethylamine, dimethylaminopropylamine, 3-amino-3-methyl-but-1-yne, 2-hydroxyethyl 2'-aminoethyl ether, 3-aminopropanol, 3,3-dimethoxy-2-propylamine, 3-methylamino-1-propylamine, methyl anthranilate and cyclohexylamine. Ammonia is advantageously used in aqueous solution.

The stated four starting materials are advantageously employed in the stoichiometric ratio, i.e. in a molar ratio of 1:1:1:1. Deviations from these molar ratios are possible but offer no advantage.

The reaction is carried out in an aqueous medium at from 20° to 150° C., preferably from 70° to 120° C. In some cases it is advantageous to add, as a solubilizing agent, a solvent which does not react with the starting materials under the reaction conditions, such as a water-miscible alcohol. Specific examples of suitable solubilizing agents are ethanol, methanol and propanol.

After the reaction, which as a rule is complete in about 30 minutes, the reaction mixture is worked up, for example by distillation or extraction, in order to isolate the imidazoles.

Using the novel process, the 1-substituted imidazoles can be prepared smoothly and in good yield. Surprisingly, only small amounts of the 1-unsubstituted imidazoles are formed at the same time. The products are valuable intermediates, for example for the preparation of drugs or crop protection agents.

EXAMPLE 1

Preparation of 1-methylimidazole

A mixture of 145 parts of 40% strength aqueous glyoxal solution and 75 parts of 40% strength aqueous formaldehyde solution, and a mixture of 382.5 parts of 4.4% strength aqueous ammonia and 77.5 parts of 40% strength aqueous methylamine solution are themselves mixed for 30 minutes in a stirred flask at 70° C. After completion of the addition, stirring is continued for 30 minutes at 70° C. The reaction mixture is then worked up by distillation. 67.8 parts of 98.5% pure N-methylimidazole (boiling point 63°–65° C./3 mm Hg) are obtained, corresponding to a yield of 81.4%.

EXAMPLE 2

Preparation of 1-phenylimidazole:

A mixture of 93.1 parts of aniline and 68 parts of 25% strength aqueous ammonia in 100 parts of propanol, and a mixture of 145 parts of 40% strength aqueous glyoxal solution and 75 parts of 40% strength aqueous formaldehyde solution are simultaneously stirred into 200 parts of propanol in the course of 30 minutes, at 80° C. The mixture is then kept at 80° C. for a further 30 minutes. Thereafter the solvent is stripped off under reduced pressure and the residue is subjected to fractional distillation. 100.9 parts of N-phenylimidazole (boiling point 128° C./2 mm Hg) are obtained, corresponding to a yield of 70.0%.

EXAMPLE 3

Preparation of 1-octylimidazole 64.6 parts of n-octylamine and 34 parts of 25% strength aqueous ammonia are dissolved in 186 parts of propanol and are introduced dropwise over 30 minutes, simultaneously with a mixture of 72.5 parts of 40% strength aqueous glyoxal solution and 37.5 parts of 40% strength aqueous formaldehyde solution, into a stirred flask. The temperature is kept at 65° C. After all has been introduced, stirring is continued for 20 minutes at 65° C., and the mixture is then worked up by distillation. 64.2 parts of 1-octylimidazole (boiling point 110° C./1 mm Hg) are obtained, corresponding to a yield of 71.3% of theory.

EXAMPLE 4

Preparation of 1-methylimidazole

A mixture of 145 parts of 40% strength aqueous glyoxal solution and 75 parts of 40% strength aqueous formaldehyde solution, and a mixture of 77.5 parts of 40% strength aqueous methylamine solution and 382.5 parts of 4.4% strength aqueous ammonia are introduced simultaneously, over 30 minutes, into 100 parts of water in an autoclave at 110° C. After a further 30 minutes at 110° C., the mixture is worked up by distillation. 76.8 parts of 1-methylimidazole, corresponding to 93.7% of theory, are obtained.

EXAMPLE 5

Preparation of 1,4,5-trimethylimidazole 88 parts of diacetyl and 75 parts of 40% strength aqueous formaldehyde solution are dissolved in 50 parts of propanol and, simultaneously with a mixture of 77.5 parts of 40% strength aqueous methylamine solution and 170 parts of 10% strength aqueous ammonia, are stirred into 100 parts of propanol, at 70° C., in the course of 30 minutes. After a further 30 minutes at 70° C., the mixture is worked up by distillation. 63.6 parts of 1,4,5-trimethylimidazole (boiling point 73° C./3 mm Hg), corresponding to a yield of 57.8% of theory, are obtained.

EXAMPLE 6

Preparation of 1-dodecylimidazole 92.5 parts of dodecylamine and 34 parts of 25% strength aqueous ammonia are dissolved in 100 parts of propanol and are added dropwise, in the course of 30 minutes, simultaneously with a mixture of 72.5 parts of 40% strength aqueous glyoxal solution and 37.5 parts of 40% strength aqueous formaldehyde solution, to 200 parts of propanol at 80° C. The mixture is then stirred for a further 20 minutes. Working up by distillation gives 76.5 parts of N-dodecylimidazole (boiling point 152° C./2 mm Hg), corresponding to 64.8% of theory.

EXAMPLE 7

Preparation of 1,2,4,5-tetramethylimidazole

A mixture of 86 parts of diacetyl and 44 parts of acetaldehyde, and a mixture of 77.5 parts of 40% strength aqueous methylamine solution and 68 parts of 25% strength aqueous ammonia, are simultaneously added dropwise, over 30 minutes, to 300 parts of propanol, at 50° C. After a further 30 minutes at 50° C., the mixture is worked up by distillation. 52 g of 1,2,4,5-tetramethylimidazole (boiling point 110°/1.5 mm Hg), corresponding to 45.4% of theory, are obtained.

EXAMPLE 8

Preparation of 1-(3,3-dimethyl-prop-1-yn-1-yl)-imidazole

A mixture of 83 parts of 3-amino-3-methyl-but-1-yne and 170 parts of 10% strength aqueous ammonia, and a mixture of 145 parts of 40% strength aqueous glyoxal solution and 75 parts of 40% strength aqueous formaldehyde solution, are simultaneously added dropwise, over 20 minutes, to 100 parts of water, whilst stirring, at 50° C. After all has been added, the mixture is stirred for a further 30 minutes at 50° C. and is then worked up by distillation. 77.2 g of 1-(3,3-dimethyl-prop-1-yn-1-yl)-imidazole (boiling point 118°/15 mm Hg), corresponding to a yield of 66.0% of theory, are obtained.

EXAMPLE 9

Preparation of 1-(2''-hydroxyethoxy-1'-ethyl)-imidazole

A mixture of 105 parts of 2-hydroxyethyl 2'-aminoethyl ether and 170 parts of 10% strength aqueous ammonia, and a mixture of 145 parts of 40% strength aqueous glyoxal solution and 75 parts of 40% strength aqueous formaldehyde solution are stirred simultaneously into 100 parts of water, at 70° C. The mixture is then stirred for a further 30 minutes at 70° C. Working up by distillation gives 131 parts of 1-(2'-hydroxyethoxy-1-ethyl)-imidazole (boiling point 165°/1 mm Hg), corresponding to a yield of 84.0%.

EXAMPLE 10

Preparation of 1-(3-hydroxy-prop-1-yl)-imidazole

A mixture of 75 parts of 3-amino-propan-1-ol and 170 parts of 10% strength aqueous ammonia, and a mixture of 145 parts of 40% strength aqueous glyoxal solution and 75 parts of 40% strength aqueous formaldehyde solution, are simultaneously added dropwise, over 30 minutes, to 100 parts of water, whilst stirring, at 70° C. After stirring for a further 30 minutes at 70° C., the mixture is worked up by distillation. 77.8 parts of 1-(3-hydroxy-prop-1-yl)-imidazole (boiling point 154°/1 mm Hg), corresponding to 61.7% of theory, are obtained.

EXAMPLE 11

Preparation of 1-(3,3-dimethoxy-prop-2-yl)-imidazole

A mixture of 119 parts of 3,3-dimethoxy-propyl-2-amine and 170 parts of 10% strength aqueous ammonia is reacted with a mixture of 145 parts of 40% strength aqueous glyoxal solution and 75 parts of 40% strength aqueous formaldehyde solution, under the same conditions as in Example 10. Distillation of the reaction mixture gives 133 parts of 1-(3,3-dimethoxy-prop-2-yl)-imidazole (boiling point 124°/5 mm Hg), corresponding to a yield of 78.3% of theory.

EXAMPLE 12

Preparation of 1-(3-methylamino-prop-1-yl)-imidazole

A mixture of 176 parts of 3-methylamino-propyl-1-amine, 200 parts of water and 107 parts of ammonium chloride, and a mixture of 290 parts of 40% strength aqueous glyoxal solution and 150 parts of 40% strength formaldehyde solution are stirred simultaneously, over 30 minutes, into 100 parts of water at 70° C. Stirring is continued for 20 minutes and the mixture is then neutralized with 200 parts of 40% strength aqueous sodium hydroxide solution and is worked up by distillation. 115.6 parts of 1-(3-methylamino-prop-1-yl)-imidazole (boiling point 125°/2 mm Hg), corresponding to a yield of 41.5% of theory, are obtained.

EXAMPLE 13

Preparation of 1-(2-ethoxy-eth-1-yl)-imidazole

A mixture of 89 parts of 2-ethoxy-ethyl-1-amine and 461 parts of 3.7% strength aqueous ammonia, and a mixture of 145 parts of 40% strength aqueous glyoxal solution and 75 parts of 40% strength aqueous formaldehyde solution are reacted under the same conditions as described in Example 10. Working up by distillation gives 96.2 parts of 1-(2-ethoxy-eth-1-yl)-imidazole (boiling point 82°/1 mm Hg), corresponding to a yield of 68.7%.

We claim:

1. A process for the preparation of imidazoles of the formula

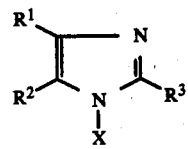

where $R^1$ and $R^2$ are hydrogen, straight-chain or branched alkyl of 1 to 5 carbon atoms, phenyl or naphthalene which alkyl, phenyl and naphthyl may be substituted by HO—, $H_3COOC$— or $H_3CO$—groups, $R^3$ is hydrogen, straight-chain or branched alkyl of 1 to 8 carbon atoms which may be substituted by phenyl or HO—, $H_3COOC$— or $H_3CO$—groups, or phenyl which may be substituted by alkyl, HO— or $H_3COOC$—groups, X is a straight-chain or branched, saturated or unsaturated hydrocarbon radical of 1 to 20 carbon atoms which may be substituted by HO—, $CH_3$—NH—, $(CH_3)_2N$—, $H_5C_2NH$—, $H_5C_2O$—, $H_3CO$— or ether groups, or is a cycloaliphatic radical or is a phenyl radical which may be substituted by $H_3CO$—, $(CH_3)_2N$—, $H_5C_2NH$— or $H_3COOC$—groups, wherein an α-dicarbonyl compound of the formula $$R^1\text{—CO—CO—}R^2,$$

ammonia, an aldehyde of the formula $R^3$—COH and a primary amine of the formula X—$NH_2$ are reacted in one step at from 20° to 150° C.

2. The process of claim 1, wherein the α-dicarbonyl compound used is glyoxal, diacetyl, benzil or methylglyoxal.

3. The process of claim 2, wherein the aldehyde used is formaldehyde, acetaldehyde, propionaldehyde, isobutyraldehyde or benzaldehyde.

* * * * *